United States Patent [19]
Bally et al.

[11] Patent Number: 5,705,385
[45] Date of Patent: Jan. 6, 1998

[54] LIPID-NUCLEIC ACID PARTICLES PREPARED VIA A HYDROPHOBIC LIPID-NUCLEIC ACID COMPLEX INTERMEDIATE AND USE FOR GENE TRANSFER

[75] Inventors: Marcel B. Bally, Bowen Island; Yuan-Peng Zhang; Dorothy L. Reimer, both of Vancouver; Jeffery J. Wheeler, Richmond, all of Canada

[73] Assignee: Inex Pharmaceuticals Corporation, Vancouver, Canada

[21] Appl. No.: 485,458

[22] Filed: Jun. 7, 1995

[51] Int. Cl.$^6$ .................................................. C12N 15/85
[52] U.S. Cl. ...................... 435/320.1; 264/4.1; 536/23.1
[58] Field of Search .............................. 424/450, 423, 424/19; 435/172.3, 320.1; 427/2.14; 264/4.1; 536/23.1; 514/44; 564/197

[56] References Cited

U.S. PATENT DOCUMENTS

| | | | |
|---|---|---|---|
| 4,394,448 | 7/1983 | Szoka, Jr. et al. | 435/172.3 |
| 4,438,052 | 3/1984 | Weder et al. | 264/4.6 |
| 4,515,736 | 5/1985 | Deamer | 424/1.21 |
| 4,598,051 | 7/1986 | Papahadjopoulos et al. | 435/172.3 |
| 4,897,355 | 1/1990 | Eppstein et al. | 435/172.3 |
| 5,171,678 | 12/1992 | Behr et al. | 435/172.3 |
| 5,208,036 | 5/1993 | Eppstein et al. | 424/450 |
| 5,264,618 | 11/1993 | Felgner et al. | 560/224 |
| 5,279,833 | 1/1994 | Rose | 424/450 |
| 5,283,185 | 2/1994 | Epand et al. | 435/172.3 |
| 5,320,906 | 6/1994 | Eley et al. | 428/402.2 |
| 5,545,412 | 8/1996 | Eppstein et al. | 424/450 |

FOREIGN PATENT DOCUMENTS

| | | | |
|---|---|---|---|
| WO 93/16024 | 10/1991 | WIPO | A61F 13/00 |
| WO 93/05162 | 3/1993 | WIPO | C12N 15/63 |
| WO 93/12756 | 7/1993 | WIPO | |
| WO 95/02698 | 1/1995 | WIPO | C12N 15/88 |
| WO 96/10390 | 4/1996 | WIPO | A61K 9/127 |

OTHER PUBLICATIONS

Hawley-Nelson, et al. *Focus* 15(3):73 (1993) Lipofectamine™Reagent: A New,Higher Efficiency Polycationic Liposome Transfection Reagent.
Stamatatos, et al., *Biochemistry* 27:3917–3925 (1988), Interactions of Cationic Lipid Vesicles With Negatively Charged Phospholipid Vesicles and Biological Membranes.
Leventis, et al., *Biochem. Biophys. Acta* 1023:124 (1990), Interactions of Mammalian Cells with Lipid Dispersions Containing Novel Metabolizable Cationic Amphiphiles.
Ballas, et al., *Biochim. Biophys. Acta* 939:8–18 (1988).
Duzgunes, *Subcellular Biochemistry* 11:195–286 (1985).
Legendre, *Pharm. Res.* 9:1235–1242 (1992).
Woodle, et al., *Biochim. Biophys. Acta* 1105:193–200 (1992), Versatility in Lipid Compositions Showing Prolonged Circulation with Sterically Stabilized Liposome.
Hofland, et al., *Proc. Natl. Acad Sci.*, 93:7305–7309 (1996), Formation of Stable Cationic Lipid/DNA Complexes for Gene Transfer.
Culver, Gene Therapy: A Handbook for Physicians, Mary-Ann Liebert, Inc. publishers, pp. 33–40 (1994).
Behr, Acc. Chem. Res. 26:274–78 (1993).
Gao, et al. Biochem, Biophys. Res. Comm. 179:280–285 (1991); DDAB.
Juliano, Biochem. Biophys. Res. Commun. 63:651 (1975).
Zhu, et al., Science 261:209–211 (1993).
Hyde et al., Nature 362:250–255 (1993).
Brigham, et al. Am. J. Med. Sci. 298:278–281 (1989).
Felgner, et al., Proc. Natl. Acad. Sci, USA 84:7413–7417 (1987).
Wilson, et al., Biochemistry 18:2192–2196 (1979).
Gershon, et al., Biochemistry 32:7143–7151 (1993).
Szoka et al.,, Ann. Rev. Biophys. Bioeng. 9:467–508 (1980).

*Primary Examiner*—James Ketter
*Assistant Examiner*—Irem Yucel
*Attorney, Agent, or Firm*—Townsend and Townsend and Crew LLP

[57] ABSTRACT

Novel, hydrophobic lipid-nucleic acid complexes. The complexes are charge-neutralized and contain the nucleic acid in a non-condensed form. Manipulation of these complexes in either detergent-based or organic solvent-based systems leads to particle formation. Thus, the present invention also provides methods of preparing lipid-nucleic acid particles which are useful for the therapeutic delivery of nucleic acids. The particles are constructed via hydrophobic lipid-nucleic acid intermediates (or complexes). Upon removal of a solubilizing component (i.e., detergent or an organic solvent) the nucleic acid forms a particle with lipids and is protected from degradation. The particles thus formed are suitable for use in intravenous nucleic acid transfer as they are stable in circulation, of a size required for pharmacodynamic behavior resulting in access to extravascular sites and target cell populations.

3 Claims, 11 Drawing Sheets

LIPID-NUCLEIC ACID PARTICLES PREPARED VIA A HYDROPHOBIC LIPID-NUCLEIC ACID COMPLEX INTERMEDIATE AND USE FOR GENE TRANSFER

FIELD OF THE INVENTION

This invention relates to methods of preparing lipid-nucleic acid particles which are useful for the introduction of nucleic acids into cells. The lipid-nucleic acid particles prepared by this method are stable in vivo and are suitable as nucleic acid or antisense transfer delivery vehicles, practical for clinical use.

BACKGROUND OF THE INVENTION

Developments in recombinant deoxyribonucleic acid ("DNA") technology have opened up new avenues for medical treatment. The location and sequences of an increasing number of disease-related genes are being identified, and clinical testing of nucleic acid-based therapeutics for a variety of diseases is now underway.

Gene therapy involves the introduction of genetic material into a cell to facilitate expression of a deficient or defective protein. Missing or defective genes (sequences of DNA encoding messenger RNA which are used as templates for protein construction) which are responsible for the production of these proteins result in a class of genetic disease often referred to as 'inborn errors of metabolism'. In some cases the disease can be treated by controlling the diet, as in the case of phenylketonuria, in which the liver enzyme responsible for the conversion of phenylalanine to tyrosine is defective. Untreated, this disease can result in mental retardation.

Treatments available for most genetic diseases are not as straightforward as merely altering the diet. For example, adenosine deaminase (ADA) deficiency results from a missing or defective gene that makes the adenosine deaminase enzyme. This enzyme is essential for a healthy immune system. ADA deficiency, however, is the disease successfully treated by the first human "gene transfer" experiment conducted by Kenneth Culver in 1990 (see, Culver, GENE THERAPY: A HANDBOOK FOR PHYSICIANS, Mary-Ann Liebert, Inc. publishers, p. 33–40 (1994)).

One method of introducing nucleic acids into a cell is mechanically, using direct microinjection. However this method is only practical for transfecting eukaryotic germline cells for the production of transgenic systems. To be effective in treating a disease, a nucleic acid-based therapy must enter many cells.

Systemic gene transfer entails distributing nucleic acids to target cells and then transferring the nucleic acid across a target cell membrane intact and in a form that can function in a therapeutic manner. In vivo gene transfer is complicated by serum interactions, immune clearance, toxicity and biodistribution.

The in vivo gene transfer methods under study in the clinic consist almost entirely of viral vectors. Although viral vectors have the inherent ability to transport nucleic acids across cell membranes and some can integrate exogenous DNA into the chromosomes, they can carry only limited amounts of DNA and also pose risks. One such risk involves the random integration of viral genetic sequences into patient chromosomes, potentially damaging the genome and possibly inducing a malignant transformation. Another risk is that the viral vector may revert to a pathogenic genotype either through mutation or genetic exchange with a wild type virus.

Lipid-based vectors have also been used in gene transfer and have been formulated in one of two ways. In one method, the nucleic acid is introduced into preformed liposomes made of mixture of cationic lipids and neutral lipids. The complexes thus formed have undefined and complicated structures and the transfection efficiency is severely reduced by the presence of serum. Preformed liposomes are commercially available as LIPOFECTIN® and LIPOFECTAMINE®. The second method involves the formation of DNA complexes with mono- or poly-cationic lipids without the presence of a neutral lipid. These complexes are prepared in the presence of ethanol and are not stable in water. Additionally, these complexes are adversely affected by serum (see, Behr, Acc. Chem. Res. 26:274–78 (1993)). An example of a commercially available poly-cationic lipid is TRANSFECTAM®.

Other efforts to encapsulate DNA in lipid-based formulations have not overcome these problems (see, Szoka, et al., Ann. Rev. Biophys. Bioeng. 9:467 (1980); and Deamer, U.S. Pat. No. 4,515,736).

Ideally, a delivery vehicle for nucleic acid will be small enough (<200 nm) and stable enough in circulation to distribute from local injection sites or following intravenous injection. The composition will have the maximum amount of nucleic acid per particle and will be homogenous and reproducible. The composition should also maintain the nucleic acid in a configuration which is protected from degradation prior to nuclear delivery and should efficiently transfect the target cells.

Surprisingly, the present invention provides such compositions and methods for their preparation.

SUMMARY OF THE INVENTION

The present invention provides novel, lipid-nucleic acid particles via formation of hydrophobic lipid-nucleic acid complexes. The complexes are charge-neutralized. Formation of these complexes in either detergent-based or organic solvent-based systems, followed by removal of the detergent or organic solvent, leads to particle formation.

Thus, the present invention also provides methods of preparing lipid-nucleic acid particles which are useful for the therapeutic delivery of nucleic acids. The particles are constructed via a hydrophobic lipid-nucleic acid intermediate (or complex). Upon removal of a solubilizing component (i.e., detergent or an organic solvent) the nucleic acid becomes protected from degradation. The particles thus formed are suitable for use in intravenous nucleic acid transfer as they are stable in circulation, of a size required for pharmacodynamic behavior resulting in access to extravascular sites and target cell populations.

Briefly, one method of forming lipid-nucleic acid particles, involves:

(a) contacting nucleic acids with a solution of non-cationic lipids and a detergent to form a nucleic acid-lipid mixture;

(b) contacting cationic lipids with the nucleic acid-lipid mixture to neutralize the negative charge of said nucleic acids and form a charge-neutralized mixture of nucleic acids and lipids; and (c) removing the detergent from the charge-neutralized mixture to provide the lipid-nucleic acid particles in which the nucleic acids are protected from degradation.

Another method of forming lipid-nucleic acid particles, involves:

(a) contacting an amount of cationic lipids with nucleic acids in a solution; the solution comprising of from about 15–35% water and about 65–85% organic solvent and the amount of cationic lipids being sufficient to produce a +/− charge ratio of from about 0.85 to about 2.0, to provide a hydrophobic, charge-neutralized lipid-nucleic acid complex;

(b) contacting the hydrophobic, charge-neutralized lipid-nucleic acid complex in solution with non-cationic lipids, to provide a lipid-nucleic acid mixture; and (c) removing the organic solvents from the lipid-nucleic acid mixture to provide lipid-nucleic acid particles in which the nucleic acids are protected from degradation.

It is a further aspect of the invention to provide in vitro and in vivo methods for treatment of diseases which involve the overproduction or underproduction of particular proteins. In these methods, a nucleic acid encoding a desired protein or blocking the production of an undesired protein, is formulated through a hydrophobic intermediate into a lipid-nucleic acid particle, and the particles are administered to patients requiring such treatment. Alternatively, cells are removed from a patient, transfected with the lipid-nucleic acid particles described herein, and reinjected into the patient.

DETAILED DESCRIPTION OF THE INVENTION

CONTENTS

I. Glossary

II. General

Figure 1:
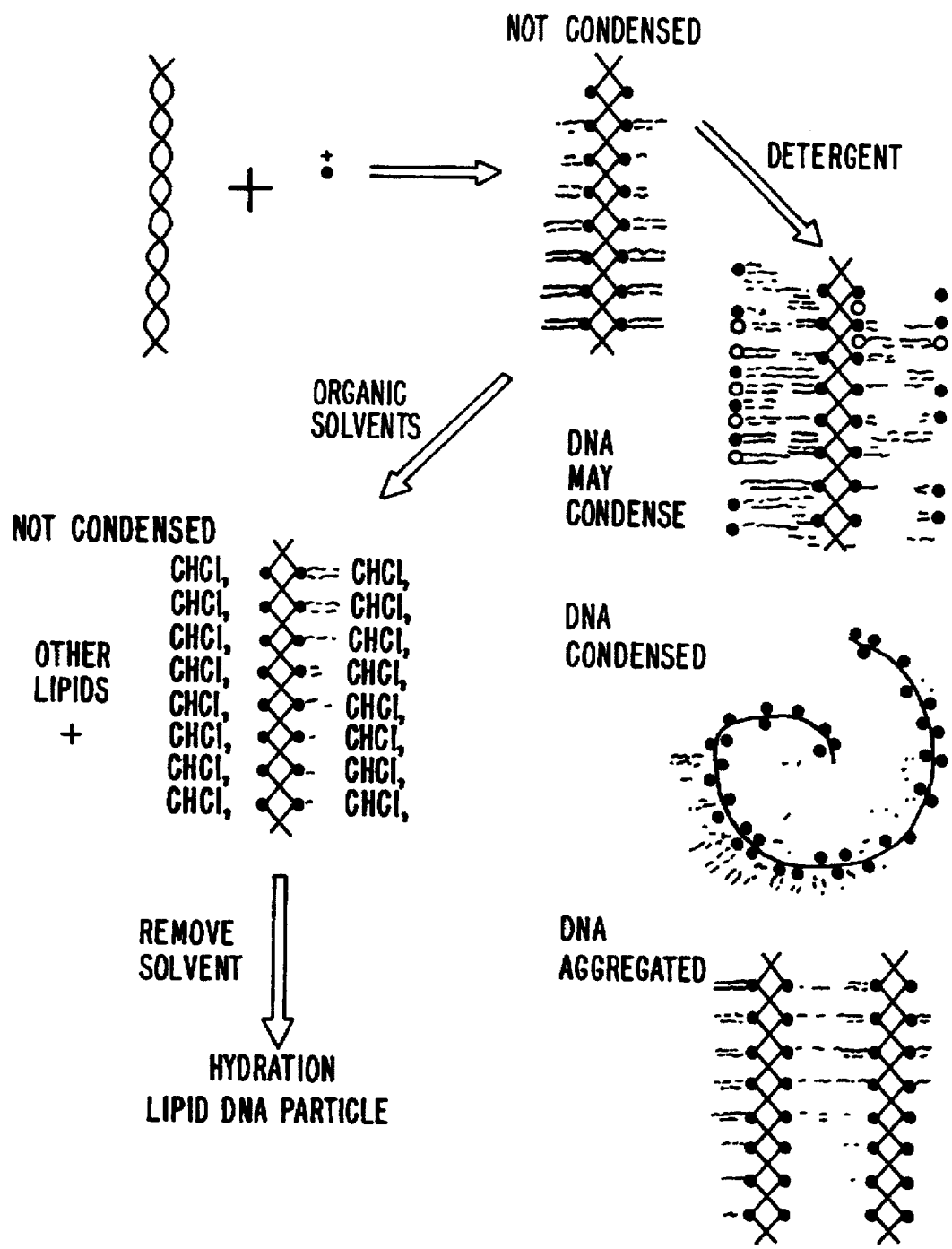
FIG. 1 is a model for the binding of monocationic lipids to nucleic acids resulting in the formation of charge-neutralized, lipid-nucleic acid complexes which are hydrophobic and in which the nucleic acid is present in an uncondensed form.

III. Methods of Formulating Lipid-Nucleic Acid Complexes and Particles

IV. Pharmaceutical Preparations

V. Administration of Lipid-Nucleic Acid Particle Formulations

VI. Examples

VII. Conclusion

I. Glossary

Abbreviations and Definitions

The following abbreviations are used herein: CHO, Chinese hamster ovary cell line; B16, murine melanoma cell line; DC-Chol, 3β-(N-(N',N'-dimethylaminoethane) carbamoyl)cholesterol (see, Gao, et al., *Biochem. Biophys. Res. Comm.* 179:280–285 (1991)); DDAB, N,N-distearyl-N,N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride (see commonly owned patent application U.S. Ser. No. 08/316,399, incorporated herein by reference); DOGS, diheptadecylamidoglycyl spermidine; DOPE, 1,2-sn-dioleoylphoshatidylethanolamine; DOSPA, N-(1-(2,3-dioleyloxy)propyl)-N-(2-(sperminecarboxamido) ethyl)-N,N-dimethylammonium trifluoroacetate; DOTAP, N-(1-(2,3-dioleoyloxy)propyl)-N,N,N-trimethylammonium chloride; DOTMA, N-(1-(2,3-dioleyloxy)propyl)-N,N,N-trimethylammonium chloride; ESM, egg sphingomyelin; RT, room temperature; TBE, Tris-Borate-EDTA (89 mM in Tris-borate and 2 mM in EDTA); HEPES, 4-(2-hydroxyethyl)-1-piperazineethanesulfonic acid; PBS, phosphate-buffered saline; EGTA, ethylenebis (oxyethylenenitrilo)-tetraacetic acid.

The term "acyl" refers to a radical produced from an organic acid by removal of the hydroxyl group. Examples of acyl radicals include acetyl, pentanoyl, palmitoyl, stearoyl, myristoyl, caproyl and oleoyl.

As used herein, the term "pharmaceutically acceptable anion" refers to anions of organic and inorganic acids which provide non-toxic salts in pharmaceutical preparations. Examples of such anions include chloride, bromide, sulfate, phosphate, acetate, benzoate, citrate, glutamate, and lactate. The preparation of pharmaceutically acceptable salts is described in Berge, et al., *J. Pharm. Sci.* 66:1–19 (1977), incorporated herein by reference.

The term "lipid" refers to any suitable material resulting in a bilayer such that a hydrophobic portion of the lipid material orients toward the bilayer while a hydrophilic portion orients toward the aqueous phase. Amphipathic lipids are necessary as the primary lipid vesicle structural element. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s). The preferred amphipathic compounds are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine could be used. Other compounds lacking in phosphorus, such as sphingolipid and glycosphingolipid families are also within the group designated as lipid. Additionally, the amphipathic lipids described above may be mixed with other lipids including triglycerides and sterols.

The term "neutral lipid" refers to any of a number of lipid species which exist either in an uncharged or neutral zwitterionic form at physiological pH. Such lipids include, for example diacylphosphatidylcholine, diacylphosphatidylethanolamine, ceramide, sphingomyelin, cephalin, and cerebrosides.

The term "non-cationic lipid" refers to any neutral lipid as described above as well as anionic lipids. Examples of anionic lipids include cardiolipin, diacylphosphatidylserine and diacylphosphatidic acid.

The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

The term "transfection" as used herein, refers to the introduction of polyanionic materials, particularly nucleic acids, into cells. The term "lipofection" refers to the introduction of such materials using liposome complexes. The polyanionic materials can be in the form of DNA or RNA which is linked to expression vectors to facilitate gene expression after entry into the cell. Thus the polyanionic material used in the present invention is meant to include DNA having coding sequences for structural proteins, receptors and hormones, as well as transcriptional and translational regulatory elements (i.e., promoters, enhancers, terminators and signal sequences) and vector sequences. Methods of incorporating particular nucleic acids into expression vectors are well known to those of skill in the art, but are described in detail in, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

"Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

The term "hydrophobic" as applied to DNA and DNA complexes, refers to complexes which are substantially more soluble in organic solvents than in aqueous solutions. More particularly, hydrophobic DNA and DNA complexes are those which are at least 50% soluble in organic solvents such as chloroform/methanol mixtures, and preferably more than 70% soluble, more preferably more than 90% soluble in such organic solvents.

II. General

The present invention provides lipid-nucleic acid particles produced via novel, hydrophobic nucleic acid-lipid intermediate complexes. The complexes are charge-neutralized. Manipulation of these complexes in either detergent-based or organic solvent-based systems can lead to particle formation in which the nucleic acid is protected and in which particle components can be altered to improve transfection efficiencies in vitro and in vivo. Gene delivery in vitro can be improved, for example, through incorporation of a lipid, such as biotinylated phospholipids, that can facilitate targeting via avidin linked monoclonal antibodies. In vivo pharmacokinetic properties can be improved for example, by i) incorporation of cholesterol, ii) control of particle size, iii) elimination of surface charge and/or iv) incorporation of lipids (e.g., PEG-modified lipids) that reduce protein binding and reticuloendothelial cell uptake.

Although directed to the transfer of nucleic acid, the particles and method of formulating the particles can be used for delivering essentially any polyanionic molecule including nucleic acid. As noted in the Background of the Invention, typical lipid-nucleic acid formulations are formed by combining the nucleic acid with a preformed cationic liposome (see, U.S. Pat. Nos. 4,897,355, 5,264,618, 5,279,833 and 5,283,185). In such methods, the nucleic acid is attracted to the cationic surface charge of the liposome, thereby forming a heterogeneous aggregate. This aggregation is typically associated with the charge neutralization which occurs upon mixing polyanionic nucleic acids with polyvalent cations.

The present invention also provides methods of forming lipid-nucleic acid particles, however, the nucleic acid is not condensed during the intermediate stages of particle formation. Additionally, the particles formed in the present invention are preferably neutral or negatively-charged at physiological pH. For in vivo applications, neutral particles are particularly preferred, while for in vitro applications the particles are more preferably negatively charged. This provides the further advantage of reduced aggregation over the positively-charged liposome formulations in which a nucleic acid can be encapsulated in cationic lipids. Still further, the particles formed in the present invention provide significantly enhanced protection of the nucleic acid against degradation by DNases, compared to earlier methods.

III. Methods of Formulating Lipid-Nucleic Acid Complexes and Particles

In one aspect, the present invention provides novel, lipid-nucleic acid complexes consisting essentially of cationic lipids and nucleic acids. These complexes can be distinguished from other complexes by several features. In particular, these complexes have a hydrophobic character (being soluble in organic solvents) and are charge-neutralized. Additionally, the nucleic acid portion of the complexes exists in an uncondensed form. These complexes can be used in the preparation of the lipid-nucleic acid particles which are described below and which are themselves useful for transfecting cells in vitro or in vivo.

The complexes consist essentially of cationic lipids and nucleic acids. The cationic lipids can be any of a number of lipid species which carry a net positive charge at physiological pH, including, for example DODAC, DOTMA, DDAB, DOTAP, DOSPA, DC-Chol, DOGS and DMRIE. Additionally, a number of commercial preparations of cationic lipids are available which can be used in the present invention. These include, for example, LIPOFECTIN®; LIPOFECTAMINE® and TRANSFECTAM®.

The nucleic acids which are useful in the present invention (including both the complexes and particles) are typically nucleotide polymers having from 10 to 100,000 nucleotide residues. Typically, the nucleic acids are to be administered to a subject for the purpose of repairing or enhancing the expression of a cellular protein. Additionally, the nucleic acid can carry a label (e.g., radioactive label, fluorescent label or colorimetric label) for the purpose of providing clinical diagnosis relating to the presence or absence of complementary nucleic acids. Accordingly, the nucleic acids, or nucleotide polymers, can be polymers of nucleic acids including genomic DNA, cDNA, mRNA or oligonucleotides containing nucleic acid analogs, for example, the antisense derivatives described in a review by Stein, et al., *Science* 261:1004–1011 (1993) and in U.S. Pat. Nos. 5,264,423 and 5,276,019, the disclosures of which are incorporated herein by reference. Still further, the nucleic acids may encode transcriptional and translational regulatory sequences including promoter sequences and enhancer sequences.

The nucleotide polymers can be single-stranded DNA or RNA, or double-stranded DNA or DNA-RNA hybrids. Examples of double-stranded DNA include structural genes, genes including control and termination regions, and self-replicating systems such as plasmid DNA.

Single-stranded nucleic acids include antisense oligonucleotides (complementary to DNA and RNA), ribozymes and triplex-forming oligonucleotides. In order to increase stability, some single-stranded nucleic acids will preferably have some or all of the nucleotide linkages substituted with stable, non-phosphodiester linkages, including, for example, phosphorothioate, phosphorodithioate, phosphoroselenate, or O-alkyl phosphotriester linkages.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

Multiple genetic sequences can be also be used in the present methods. Thus, the sequences for different proteins may be located on one strand or plasmid. Promoter, enhancer, stress or chemically-regulated promoters, antibiotic-sensitive or nutrient-sensitive regions, as well as therapeutic protein encoding sequences, may be included as required. Non-encoding sequences may be also be present, to the extent that they are necessary to achieve appropriate expression.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., *Tetrahedron Lett.*, 22:1859–1862 (1981); Matteucci, et al., *J. Am. Chem. Soc.*, 103:3185–3191 (1981); Caruthers, et al., *Genetic Engineering*, 4:1–17 (1982); Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984) which are incorporated herein by reference.

The formation of the lipid-nucleic acid complexes can be carried out either in a monophase system (e.g., a Bligh and Dyer monophase or similar mixture of aqueous and organic solvents) or in a two phase system with suitable mixing.

When formation of the complexes is carried out in a monophase system, the cationic lipids and nucleic acids are each dissolved in a volume of the monophase mixture. Combination of the two solutions provides a single mixture in which the complexes form. Alternatively, the complexes can form in two-phase mixtures in which the cationic lipids bind to the nucleic acid (which is present in the aqueous phase), and "pull" it in to the organic phase. Without intending to be bound by any particular theory of formation, FIG. 1 provides a model for the binding of monocationic lipids to DNA which results in the formation of a hydrophobic (organic-soluble) lipid-nucleic acid complex. In this figure, cationic lipids first bind to the DNA to form a complex in which the DNA is uncondensed. This complex is soluble in the organic phase or in a monophase and the DNA remains uncondensed. Upon the addition of other lipids and removal of solvent, and hydration, the complexes form particles (described in more detail below).

In another aspect, the present invention provides a method for the preparation of lipid-nucleic acid particles, comprising:

(a) contacting nucleic acids with a solution comprising non-cationic lipids and a detergent to form a nucleic acid-lipid mixture;

(b) contacting cationic lipids with the nucleic acid-lipid mixture to neutralize a portion of the negative charge of the nucleic acids and form a charge-neutralized mixture of nucleic acids and lipids; and (c) removing the detergent from the charge-neutralized mixture to provide the lipid-nucleic acid particles in which the nucleic acids are protected from degradation.

Figure 2:
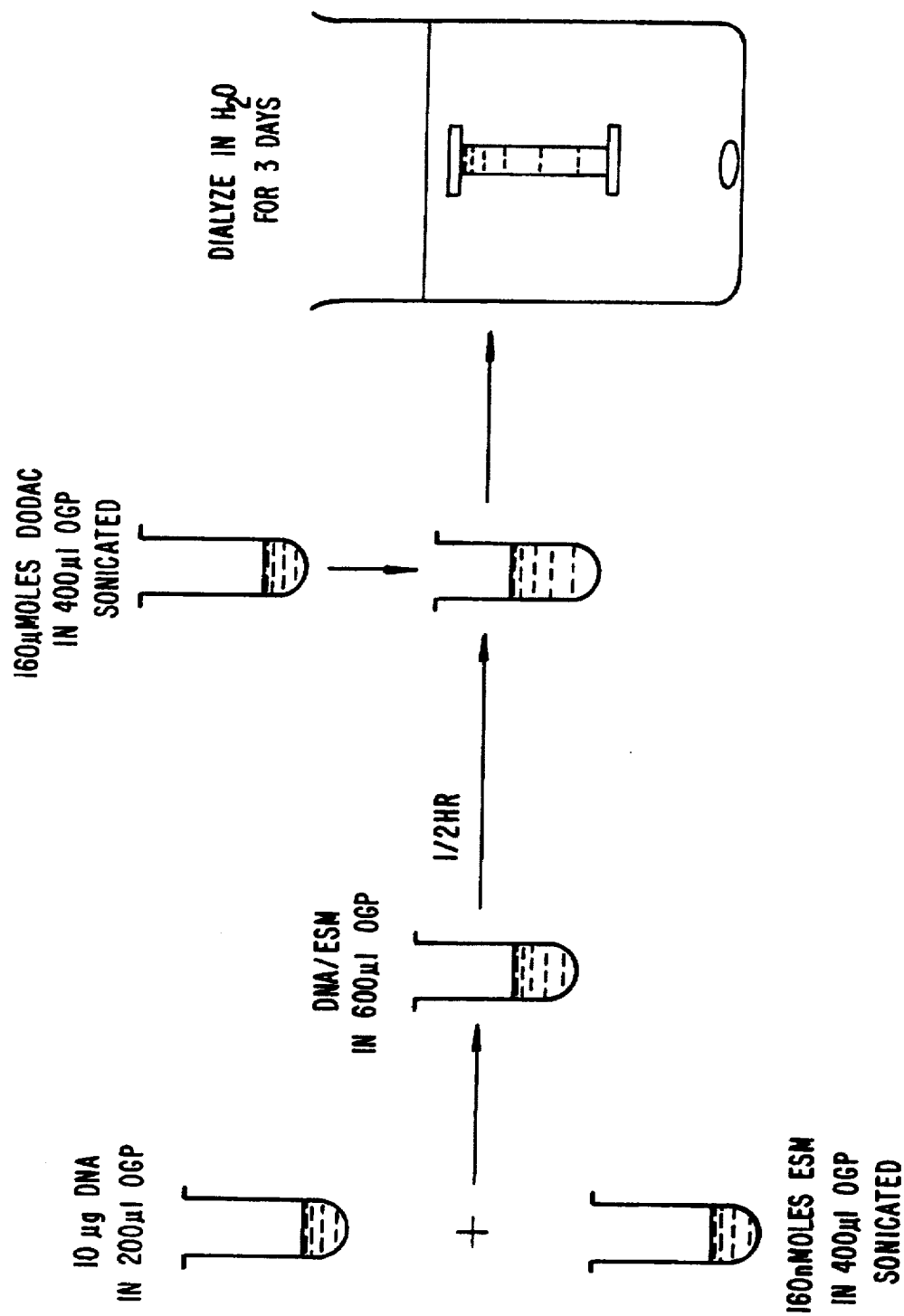
FIG. 2 illustrates a protocol for preparing lipid-nucleic acid particles using detergent dialysis.

Without intending to be limited by any particular aspect of the illustration, FIG. 2 provides a depiction of one method of forming the particles using detergent dialysis. In this figure, DNA in an aqueous detergent solution (OGP) is combined with non-cationic lipids (ESM) in an aqueous detergent solution and allowed to anneal for about 30 min. A previously sonicated mixture of cationic lipid (DODAC) in detergent is added and the resulting mixture is dialyzed for 3 days to remove detergent and thereby form lipid-nucleic acid particles. One of skill in the art will understand that for the kinetic formation of such particles, the order of addition of cationic lipids and non-cationic lipids could be reversed, or the lipids could be added simultaneously.

The nucleic acids used in this aspect of the invention can be any of those described for the above complexes. In preferred embodiments, the nucleic acid is a plasmid.

The non-cationic lipids used in the present invention can be any of a variety of neutral uncharged, zwitterionic or anionic lipids. Examples of neutral lipids which are useful in the present methods are diacylphosphatidylcholine, diacylphosphatidylethanolamine, ceramide, sphingomyelin, cephalin, and cerebrosides. Other lipids such as lysophosphatidylcholine and lysophosphatidylethanolamine may be present. In preferred embodiments, the non-cationic lipids are diacylphosphatidylcholine (e.g., dioleoylphosphatidylcholine, dipalmitoylphosphatidylcholine and dilinoleoylphosphatidylcholine), diacylphosphatidylethanolamine (e.g., dioleoylphosphatidylethanolamine and palmitoyloleoylphosphatidylethanolamine), ceramide or sphingomyelin. The acyl groups in these lipids are preferably acyl groups derived from fatty acids having $C_{10}$–$C_{24}$ carbon chains. More preferably the acyl groups are lauroyl, myristoyl, palmitoyl, stearoyl or oleoyl. In particularly preferred embodiments, the non-cationic lipid will be 1,2-sn-dioleoylphosphatidylethanolamine, or egg sphingomyelin (ESM). Additionally, the non-cationic lipids will include polyethylene glycol-based polymers such as PEG 2000, PEG 5000 and polyethylene glycol conjugated to phospholipids or to ceramides (referred to as PEG-Cer), as described in co-pending U.S. Ser. No. 08/316,429, incorporated herein by reference.

The detergents which are useful in the present invention are typically one or more neutral detergents or combinations of detergents and organic solvents. The detergents are preferably, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Triton X-405; hexyl-, heptyl-, octyl- and nonyl-β-D-glucopyranoside; with octyl β-D-glucopyranoside and Tween 20 being the most preferred. The organic solvents which are useful in combination with a detergent include chloroform, dichloromethane, diethylether, cyclohexane, cyclopentane, benzene, toluene, acetone, benzyl alcohol, methanol, or other aliphatic alcohols such as propanol, isopropanol, butanol, tert-butanol, iso-butanol, pentanol and hexanol. The selection of an organic solvent will typically involve consideration of solvent polarity and the ease with which the solvent can be removed at the later stages of particle formation. Accordingly, the preferred organic solvents used in conjunction with the detergent are ethanol, dichloromethane, chloroform, methanol and diethyl ether with chloroform and methanol being the most preferred.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to 5 times the amount of cationic lipid, preferably about 0.5 to 2 times the amount of cationic lipid used.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DODAC, DOTMA, DDAB, DOTAP, DC-Chol and DMRIE. These lipids and related analogs have been described in co-pending U.S. Ser. No. 08/316,399; U.S. Pat. Nos. 5,208,036, 5,264,618, 5,279,833 and 5,283,185, the disclosures of which are incorporated herein by reference. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPO-FECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA).

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the lipid-nucleic acid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 100 nm to several microns. To achieve further size reduction or homogeneity of size in the particles, the lipid-nucleic acid particles can be sonicated, filtered or subjected to other sizing techniques which are used in liposomal formulations and are known to those of skill in the art.

In other embodiments, the methods will further comprise adding nonlipid polycations which are useful to effect the transfection of cells using the present compositions. Examples of suitable nonlipid polycations include, hexadimethrine bromide (sold under the brandname POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine and polyethyleneimine. Addition of these salts is preferably after the particles have been formed.

In another aspect, the present invention provides methods for the preparation of lipid-nucleic acid particles, comprising:

(a) contacting an amount of cationic lipids with nucleic acids in a solution; the solution comprising of from about 15–35% water and about 65–85% organic solvent and the amount of cationic lipids being sufficient to produce a +/− charge ratio of from about 0.85 to about 2.0, to provide a hydrophobic, charge-neutralized lipid-nucleic acid complex;

(b) contacting the hydrophobic, charge-neutralized lipid-nucleic acid complex in solution with non-cationic lipids, to provide a lipid-nucleic acid mixture; and (c) removing the organic solvents from the lipid-nucleic acid mixture to provide lipid-nucleic acid particles in which the nucleic acids are protected from degradation.

The nucleic acids, non-cationic lipids, cationic lipids and organic solvents which are useful in this aspect of the invention are the same as those described for the methods above which used detergents. In one group of embodiments, the solution of step (a) is a monophase. In another group of embodiments, the solution of step (a) is two-phase.

In preferred embodiments, the cationic lipids are DODAC, DDAB, DOTMA, DOSPA, DMRIE, DOGS or combinations thereof. In other preferred embodiments, the non-cationic lipids are ESM, DOPE, polyethylene glycol-based polymers (e.g., PEG 2000, PEG 5000, PEG-modified phospholipids or PEG-modified ceramides) or combinations thereof. In still other preferred embodiments, the organic solvents are methanol, chloroform, methylene chloride, ethanol, diethyl ether or combinations thereof.

In a particularly preferred embodiment, the nucleic acid is a plasmid; the cationic lipid is DODAC, DDAB, DOTMA, DOSPA, DMRIE, DOGS or combinations thereof; the non-cationic lipid is ESM, DOPE, polyethylene glycol-based polymers or combinations thereof; and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described for one aspect of the invention above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to 5 times the amount (on a mole basis) of cationic lipids which was used to provide the charge-neutralized lipid-nucleic acid complex. Preferably, the amount is from 0.5 to 2 times the amount of cationic lipids used.

In yet another aspect, the present invention provides lipid-nucleic acid particles which are prepared by the methods described above. In these embodiments, the lipid-nucleic acid particles are either net charge neutral or carry an overall charge which provides the particles with greater gene transfection activity. Preferably, the nucleic acid component of the particles is a nucleic acid which encodes a desired protein or blocks the production of an undesired protein. In particularly preferred embodiments, the nucleic acid is a plasmid, the non-cationic lipid is egg sphingomyelin and the cationic lipid is DODAC.

As noted above, the lipid-nucleic acid particles are useful for the transfection of cells, either in vitro or in vivo.

Accordingly, the present invention provides, in yet another aspect, a method for introducing a nucleic acid into a cell, comprising;

(a) preparing a lipid-nucleic acid particle according to the methods above; and (b) contacting the cell with the lipid-nucleic acid particle for a period of time sufficient to introduce the nucleic acid into the cell.

Although discussed in more detail below, preferred embodiments are those in which the lipid-nucleic acid particle comprises a plasmid, DODAC and ESM.

IV. Pharmaceutical Preparations

The lipid-nucleic acid particles of the present invention can be administered either alone or in mixture with a physiologically-acceptable carrier (such as physiological saline or phosphate buffer) selected in accordance with the route of administration and standard pharmaceutical practice.

Pharmaceutical compositions comprising the lipid-nucleic acid particles of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. In compositions comprising saline or other salt containing carriers, the carrier is preferably added following particle formation. Thus, after the particle is formed, the particle can be diluted into pharmaceutically acceptable carriers such as normal saline. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

The concentration of particles in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration. For diagnosis, the amount of particles administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, it is often desirable to include polyethylene glycol (PEG)-modified phospholipids, PEG-ceramide, or ganglioside $G_{M1}$-modified lipids to the particles. Addition of such components prevents particle aggregation and provides a means for increasing circulation lifetime and increasing the delivery of the lipid-nucleic acid particles to the target tissues. Typically, the concentration of the PEG-modified phospholipids, PEG-ceramide or $G_{M1}$-modified lipids in the particle will be about 1–15%.

Overall particle charge is also an important determinant in particle clearance from the blood. Charged liposomes and particles are typically taken up more rapidly by the reticuloendothelial system (Juliano, *Biochem. Biophys. Res. Commun.* 63:651 (1975)) and thus have shorter half-lives in the bloodstream. Particles with prolonged circulation half-lives are typically desirable for therapeutic and diagnostic uses. For instance, particles which can be maintained from 8, 12, or up to 24 hours in the bloodstream are particularly preferred.

In another example of their use, lipid-nucleic acid particles can be incorporated into a broad range of topical dosage forms including but not limited to gels, oils, emulsions and the like. For instance, the suspension containing the lipid-nucleic acid particles can be formulated and administered as topical creams, pastes, ointments, gels, lotions and the like.

The present invention also provides lipid-nucleic acid particles in kit form. The kit will typically be comprised of a container which is compartmentalized for holding the various elements of the kit. The kit will contain the compositions of the present inventions, preferably in dehydrated form, with instructions for their rehydration and administration. In still other embodiments, the particles and/or compositions comprising the particles will have a targeting moiety attached to the surface of the particle. Methods of attaching targeting moieties (e.g., antibodies, proteins) to lipids (such as those used in the present particles) are known to those of skill in the art.

Dosage for the lipid-nucleic acid particle formulations will depend on the ratio of nucleic acid to lipid and the administrating physician's opinion based on age, weight, and condition of the patient.

V. Administration of Lipid-Nucleic Acid Particle Formulations

Following formation of the lipid-nucleic acid particles, the particles can be contacted with the cells to be transfected. The particles can be adsorbed to almost any cell type. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid. Contact between the cells and the lipid-nucleic acid particles, when carried out in vitro, will take place in a biologically compatible medium. The concentration of particles can vary widely depending on the particular application, but is generally between about 1 μmol and about 10 mmol. Treatment of the cells with the lipid-nucleic acid particles will generally be carried out at physiological temperatures (about 37° C.) for periods of time of from about 1 to 48 hours, preferably of from about 2 to 4 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of preferred embodiments, a lipid-nucleic acid particle suspension is added to 60–80% confluent plated cells having a cell density of from about $10^3$ to about $10^5$ cells/mL, more preferably about $2 \times 10^4$ cells/mL. The concentration of the suspension added to the cells is preferably of from about 0.01 to 0.2 μg/mL, more preferably about 0.1 μg/mL.

Typical applications include using well known transfection procedures to provide intracellular delivery of DNA or mRNA sequences which code for therapeutically useful polypeptides. However, the compositions can also be used for the delivery of the expressed gene product or protein itself. In this manner, therapy is provided for genetic diseases by supplying deficient or absent gene products (i.e., for Duchenne's dystrophy, see Kunkel, et al., *Brit. Med. Bull.* 45(3):630–643 (1989), and for cystic fibrosis, see Goodfellow, *Nature* 341:102–103 (1989)). Other uses for the compositions of the present invention include introduction of antisense oligonucleotides in cells (see, Bennett, et al., *Mol. Pharm.* 41:1023–1033 (1992)).

Alternatively, the compositions of the present invention can also be used for the transfection of cells in vivo, using methods which are known to those of skill in the art. In particular, Zhu, et al., *Science* 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et at., *Am. J. Med. Sci.* 298:278–281 (1989), incorporated herein by reference, describes the in vivo transfection of lungs of mice with a functioning prokaryotic gene encoding the intracellular enzyme, chloramphenicol acetyltransferase (CAT).

For in vivo administration, the pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512–527 (1983); Mannino, et al., *Biotechniques* 6:682–690 (1988); Nicolau, et al., *Crit. Rev. Ther. Drug Carrier Syst.* 6:239–271 (1989), and Behr, *Acc. Chem. Res.* 26:274–278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In other methods, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid particles can also be administered in an aerosol inhaled into the lungs (see, Brigham, et al., *Am. J. Sci.* 298(4):278–281 (1989)) or by direct injection at the site of disease (Culver, HUMAN GENE THERAPY, Mary-Ann Liebert, Inc., Publishers, New York. pp. 70–71 (1994)).

The methods of the present invention may be practiced in a variety of hosts. Preferred hosts include mammalian species, such as humans, non-human primates, dogs, cats, cattle, horses, sheep, and the like.

VI. Examples

In the examples below, Examples 1–7 illustrate the formation and characterization of charge-neutralized lipid-nucleic acid intermediate complexes, in which the nucleic acid adopts hydrophobic character. In each of these examples, the term "DNA" or "plasmid" refers to the plasmid pCMVβ. Examples 8 and 9 illustrate the preparation and characterization of lipid-nucleic acid particles which are suitable for transfection of cells. Examples 10–12 illustrate the serum stability and transfecting ability of these lipid-nucleic acid particles.

Materials

Transfecting agents Lipofectin and Lipofectamine were purchased from Gibco/BRL (Grand Island, N.Y., USA). Transfectam Reagent was purchased from Promega Corp. (Madison, Wis., USA). The monocationic lipid DDAB, calcium chloride, L-lysine (free base), poly L-lysine hydrobromide (Avg. MW 52,000), n-octyl β-D-glucopyranoside (OGP) and DNase I were obtained from Sigma Chemical Company (St. Louis, Mo., USA). TO-PRO-1 (thiazole orange monomer) was obtained from Molecular Probes Inc., Eugene, Oreg., USA. The plasmid pCMVβ (GenBank accession #U02451) encoding *E. coli* β-galactosidase (β-gal), a 7.2 kb plasmid DNA reporter gene, was obtained from Clontech Laboratories, Palo Alto, Calif., USA.

β-gal DNA was propagated and purified using standard techniques (Sambrook et al., MOLECULAR CLONING, A LABORATORY MANUAL, Second Ed., Cold Spring Harbor, N.Y. (1989)). Radiolabeled DNA was used as a tracer and was generated by incorporating $^3$H-dUTP into the plasmid during bacterial growth, resulting in specific activities of ~50,000 dpm/µg of DNA.

All other chemicals used in these Examples were of reagent grade and all solvents used were HPLC grade.

Methods

Bligh and Dyer Extraction Procedure

Non-cationic lipids, cationic lipids and DNA were solubilized in chloroform:methanol:water (1:2.1:1) prior to mixing. This mixture of solvents and water is equivalent to that used in the preparation of a Bligh and Dyer monophase (Bligh and Dyer, *Can. J. Biochem. Physiol.* 37:91–97 (1959) ). Typically, DNA was added to achieve a final concentration of 10 µg/mL in solution while lipid was added at various concentrations. Trace quantities of $^3$H-plasmid DNA were added such that 2000 to 4000 dpm were present per 10 µg unlabelled DNA. The reaction mixtures were incubated at room temperature for 30 min in a total volume of 1 mL. Subsequently the Bligh and Dyer monophase was partitioned into a two phase system by the addition of water and chloroform (250 µL each). The samples were mixed by vortexing and the separation of the lower organic and upper aqueous phases was facilitated by centrifugation at 2000 rpm for 5 min at room temperature. The aqueous phase was removed and retained for scintillation counting. The solvent phase was dried using a stream of nitrogen gas, and the resulting film was resuspended in SOLVABLE® solubilizing agent (Dupont NEN, Boston, Mass., USA) and incubated at 50° C. for 1 hour. This last step was necessary to solubilize the dried DNA/lipid complex since the addition of the scintillation cocktail alone was not sufficient to dissociate the complex. PICOFLUOR® scintillant (Canberra Packard, Meriden, Conn., USA) was added to all samples and the radioactivity ($^3$H-DNA) was measured using a Packard TR 1900 Scintillation Counter (Canberra Packard).

Assays evaluating the stability of charge-neutralized, lipid-nucleic acid complexes were done in the presence of varying concentration of NaCl and OGP. Briefly, cationic lipid-nucleic acid complexes were prepared under conditions where 100% of the plasmid was expected to be recovered in the organic phase. NaCl or OGP was then added to the monophase system and incubations carried out at room temperature for 15 min. Bligh and Dyer extractions were performed as described above.

The binding of calcium, L-lysine, and poly-L-lysine to the plasmid was evaluated using a modification of the above procedure. These nonlipid cationic materials were dissolved at various concentrations in sterile distilled water and incubated with the plasmid (10 µg/mL final concentration in water) at room temperature for 30 min in a final volume of 250 µL. Reaction volumes were adjusted to 1 mL with chloroform:methanol (1:2.1) to produce a monophase. Bligh and Dyer extractions were then performed as described.

Dye Intercalation Assay

The fluorochrome TO-PRO-1 was used to evaluate the state of condensation of the plasmid in the charge-neutralized lipid-nucleic acid complex. TO-PRO-1 was used in this study due to its stable intercalation into the plasmid as well as the high sensitivity in the fluoroescence detection compared with the more common intercalator ethidium bromide (see, Hirons, et al., *Cytometry* 15:129–140 (1994)). Plasmid was dissolved in either the Bligh and Dyer monophase or in 100 mM OGP. Poly-L-lysine or DODAC were each added to 10 µg plasmid at a 1:1 charge ratio.

Agarose Gel Electrophoresis

Complexes involving plasmid and poly-L-lysine were formed at a nucleic acid concentration of 10 µg/mL and a 1:1 charge ratio in the presence of 100 mM OGP. Complexes involving the cationic lipid DODAC and plasmid were formed at a plasmid concentration of 10 µg/mL and increasing concentrations of DODAC (10 to 320 nmoles/mL). The mixtures were incubated at room temperature for 30 min prior to loading onto a 0.8% agarose gel. Electrophoresis was carried out in TBE buffer according to standard techniques (Sambrook, et al., MOLECULAR CLONING: A LABORATORY MANUAL, Second Edition, Cold Spring Harbor, N.Y. (1989)). Nucleic acids were visualized after staining the gel with ethidium bromide (0.5 µg/mL, 20 min) by photography with UV transillumination.

DNAse I Assay

To evaluate the protective effect of cationic lipids on DNA, the complexes formed in the presence of OGP were incubated with DNase I. Preformed charge-neutralized lipid-nucleic acid complexes (plasmid/DODAC; 1:1 charge ratio) were mixed with DNase I at a concentration where plasmid alone was susceptible to degradation at 37° C. for 10 min. The reactions were stopped by the addition of 25 mM EDTA and the samples were extracted using the Bligh and Dyer procedure in the presence of 150 mM NaCl. Under these conditions the charge-neutralized lipid-nucleic acid complexes dissociate and plasmid can be efficiently recovered in the aqueous fraction. This DNA was precipitated with 1/10th volume of 3M sodium acetate (pH 5.2) and 2.5 volumes of 95% EtOH and recovered by centrifugation at 14,000 g for 30 min at 4° C. The DNA pellet was resuspended in sterile distilled water and subjected to electrophoresis on a 0.8% agarose gel.

EXAMPLE 1

This example provides a comparison of cationic lipids and non-cationic lipids in effecting the formation of hydrophobic charge-neutralized lipid-nucleic acid complexes.

Figure 3:
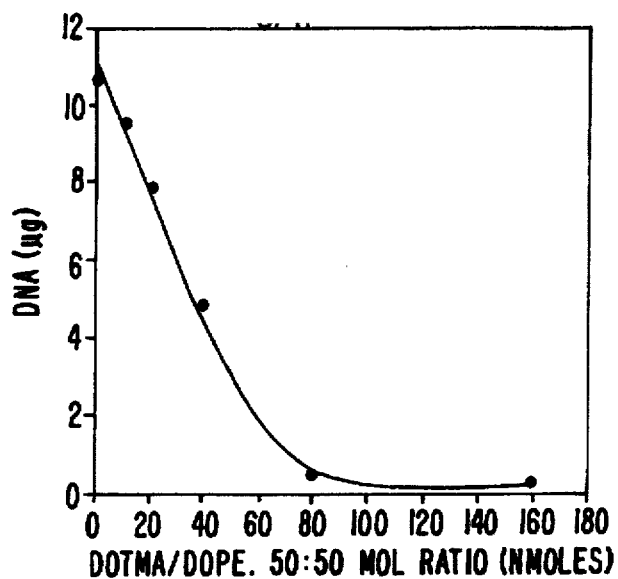
FIG. 3 shows the effect of increasing amounts of LIPO-FECTIN® (DOTMA/DOPE; 50:50 mol ratio) on the recovery of β gal plasmid DNA in the aqueous phase following Bligh and Dyer extraction of the lipid-nucleic acid complexes.

LIPOFECTIN® consists of sonicated unilamellar vesicles composed of DOTMA and DOPE (50:50 mole ratio, see, Felgner, et at., *Proc. Natl. Acad. Sci, USA* 84:7413–7417 (1987)). The liposomes are prepared in water and are provided at a total lipid concentration of 1 mg/mL. DNA (10 µg) was mixed with the liposomes in water, as described below in Example 2, to provide from 0 to 160 nmoles total lipid. Each of the mixtures was extracted using the Bligh and Dyer procedure. Surprisingly, in the presence of LIPOFECTIN®, there was a concentration dependent reduction in DNA recovered from the aqueous phase (see FIG. 3). Addition of 80 nmoles of total lipid to 10 µg DNA resulted in greater than 95% loss of DNA from the aqueous phase. This effect could not be achieved using liposomes prepared from egg phosphatidylcholine/DOPE (50:50 mole ratio). Thus, the hydrophobic complex which forms and is drawn into the organic phase is a result of the cationic lipid present in the complex.

EXAMPLE 2

This example provides a comparison of several cationic lipids in forming hydrophobic, charge-neutralized lipid-nucleic acid complexes which partition into organic solvents.

Figure 4A:
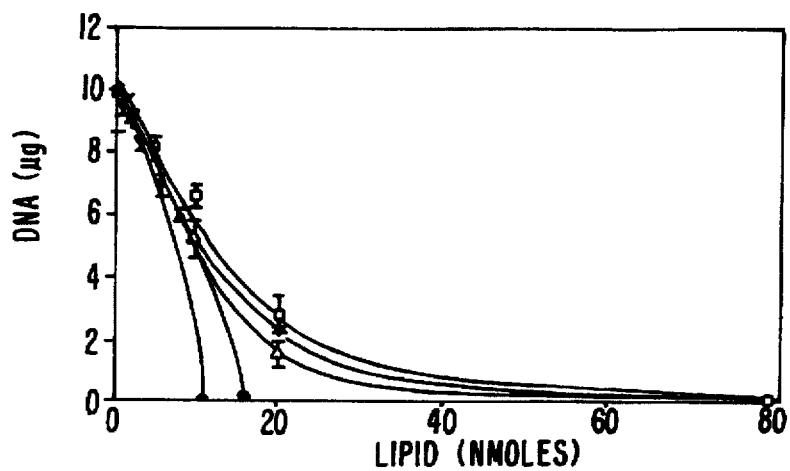
FIGS. 4A and 4B show the effect of increasing amounts of cationic lipid on the recovery of plasmid DNA in the aqueous (A) and organic (B) phase following Bligh and Dyer extraction of the lipid-nucleic acid complexes.
Figure 4B:
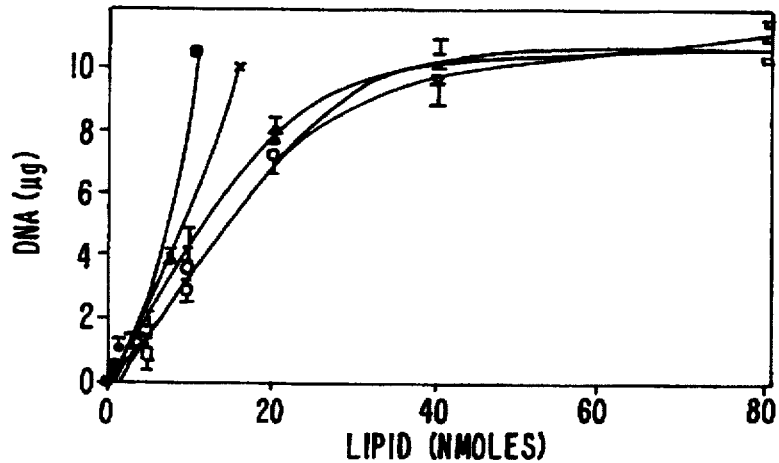

Purified monovalent cationic lipids (DOTMA, DDAB and DODAC) were each added to DNA in a Bligh and Dyer monophase solvent system. The resulting mixtures were each partitioned into two phases by the addition of water and chloroform. Plasmid DNA levels were determined in the aqueous and organic phases as described above. The results are presented in FIG. 4, and are consistent with the results presented in FIG. 3. In particular, there was found to be a cationic lipid dependent loss of DNA from the aqueous phase (FIG. 4A). There was no visible evidence of precipitated material at the aqueous/organic interface and quantification of the DNA in samples collected to include the interface did not account for appreciable DNA levels (results not shown). The DNA was found to be quantitatively transferred to the organic phase (FIG. 4B). Additionally, greater than 95% of the DNA in the monophase could be recovered in the organic phase when 40 nmoles monovalent cationic lipid was added. This value is identical to results presented in FIG. 3 in which 80 nmoles of LIPOFECTIN® (50 mol % DOTMA) resulted in the complete loss of DNA from the aqueous phase. The results presented in FIG. 4 indicate that the three different monovalent cationic lipids behave in a similar fashion under the conditions used.

EXAMPLE 3

This example illustrates the influence of multivalent cationic lipids and cationic nonlipid species on DNA partitioning into organic solvents.

LIPOFECTAMINE® (DOSPA:DOPE, 75:25 mol ratio), and TRANSFECTAM® (100% DOGS) were added to DNA (10 µg) as preformed liposomes, as described in Example 2. The liposomes contain headgroups derived from spermine and exhibit positive charges of 5 and 4, respectively at pH<7. As expected, significantly lower amounts of these lipids (calculated on the basis of moles) are required to mediate DNA partitioning into the organic phase (see FIG. 4). Complete partitioning of the DNA into the organic phase was achieved after addition of approximately 10 nmoles DOSPA and DOGS.

Figure 5A:
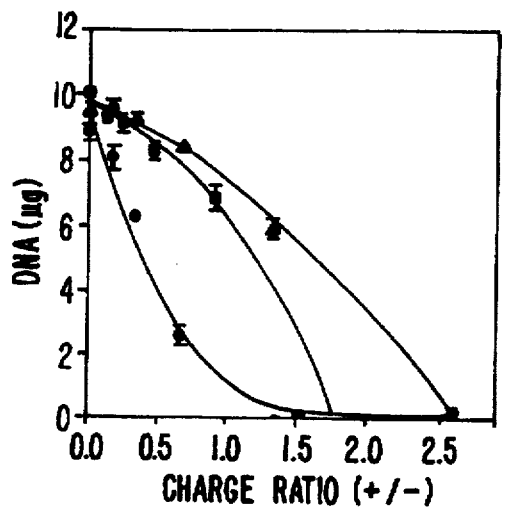
FIGS. 5A, 5B, 5C and 5D show the recovery of plasmid DNA from aqueous (A and C) and organic (B and D) fractions following Bligh and Dyer extraction and expressed as a function of charge ratio (+/−).
Figure 5C:
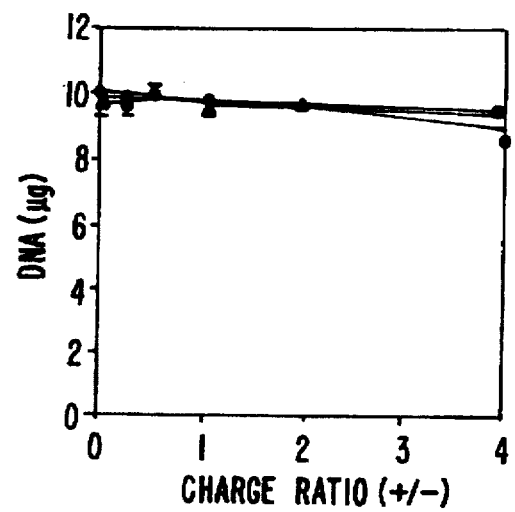
Figure 5B:
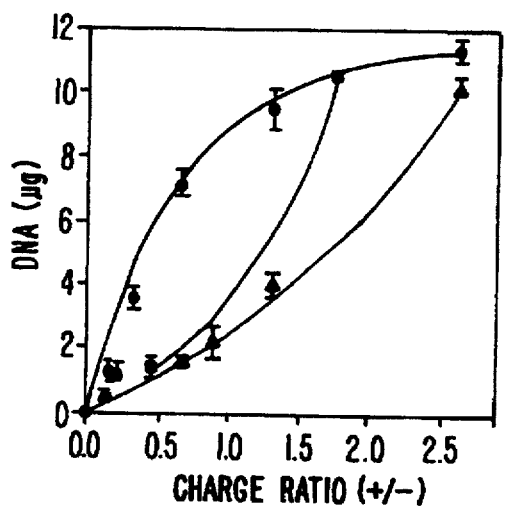
Figure 5D:
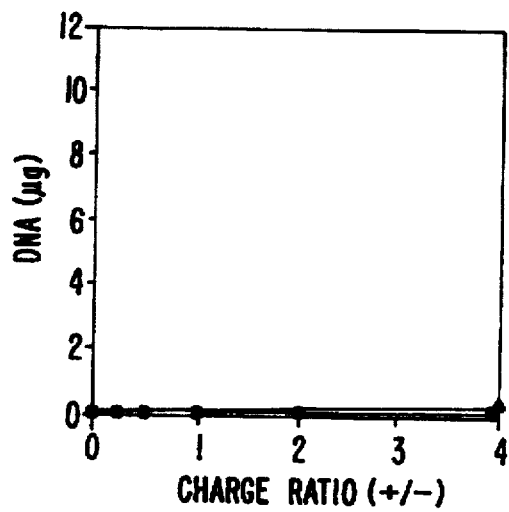

Previous studies have demonstrated that DNA condenses into small toroid or rod shaped structures when the DNA phosphate charge is at least 90% neutralized (see Wilson, et al., *Biochemistry* 18:2192–2196 (1979). The data presented in FIG. 4 was therefore expressed as a function of cation/phosphate charge ratio (FIGS. 5A and 5B). For comparison, results obtained after the addition of the nonlipid-based monovalent (lysine), divalent (calcium) and multivalent (poly-L-lysine) cations are included (FIGS. 5C and 5D). The results shown in FIG. 5 demonstrate that for monovalent cationic lipids, greater than 99% of the DNA partitioned into the organic phase when a +/− charge ratio >1 was achieved. Similar results were observed when the polyvalent lipids DOSPA and DOGS were used, although a slightly greater charge ratio was required to mediate efficient DNA transfer. However, DNA partitioning into the organic phase did not occur as a result of simple charge neutralization. When the DNA was mixed with the nonlipid cations, at charge ratios up to and in excess of 4, the majority of the DNA was invariably recovered in the aqueous phase.

EXAMPLE 4

This example illustrates that the hydrophobic, charge-neutralized lipid-nucleic acid complexes formed as described in Examples 1–3 provide the nucleic acid in an uncondensed (unprotected) configuration.

Figure 6A:
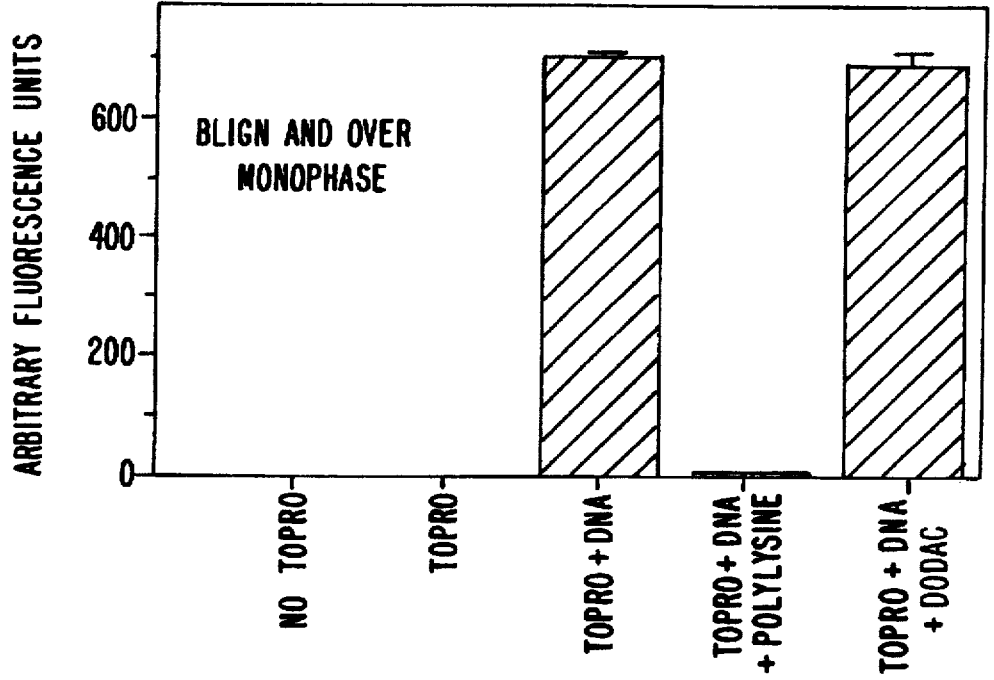
FIGS. 6A and 6B illustrate the DNA condensation by poly-L-lysine and DODAC assayed by TO-PRO-1 dye intercalation. Condensation state was assessed in a Bligh and Dyer monophase (A) and in 100 mM OGP (B).
Figure 6B:
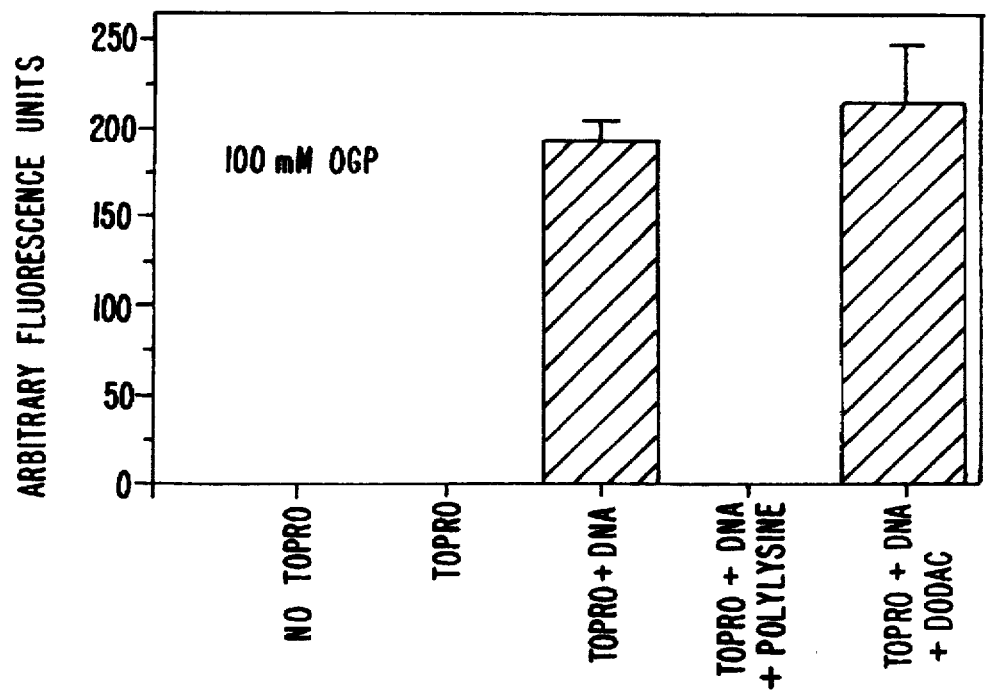

Evaluation of the hydrophobic, charge-neutralized lipid-nucleic acid complexes was carried out by assessing the ability of a small fluorescent probe to bind to the nucleic acid in the complex. This evaluation is similar to an approach using ethidium bromide (see Gershon, et al., *Biochemistry* 32:7143–7151 (1993)). TO-PRO-1 is a more sensitive, membrane impermeable, nucleic acid intercalating dye and therefore, provides a more stringent test of DNA binding. DNA was mixed with either a monovalent cationic lipid or poly-L-lysine in the Bligh and Dyer monophase (FIG. 6A). TO-PRO-1 was then added to a final concentration of 1 µM and fluorescence was measured at 533 nm (probe excitation at 509 nm). In the absence of DNA no fluorescence was observed. However, when plasmid DNA was added (10 µg/mL) there was a >600 fold increase in fluorescence at 533 nm. When TO-PRO-1 was added to the DNA/poly-1-lysine mixture, no fluorescence was observed. This is consistent with the existence of the DNA in a condensed state due to charge neutralization. In dramatic contrast, addition of TO-PRO-1 to a hydrophobic charge-neutralized lipid-nucleic acid complex (plasmid/DODAC complex), TO-PRO-1 binding was not excluded. This result is consistent with the concept that DNA within the hydrophobic complex does not exist as a condensed structure. FIG. 6B shows that similar results were obtained when TO-PRO-1 was added to plasmid DNA mixed with either poly-L-lysine or the cationic lipid DODAC in the presence of 100 mM OGP, a nonionic detergent.

EXAMPLE 5

Figure 7:
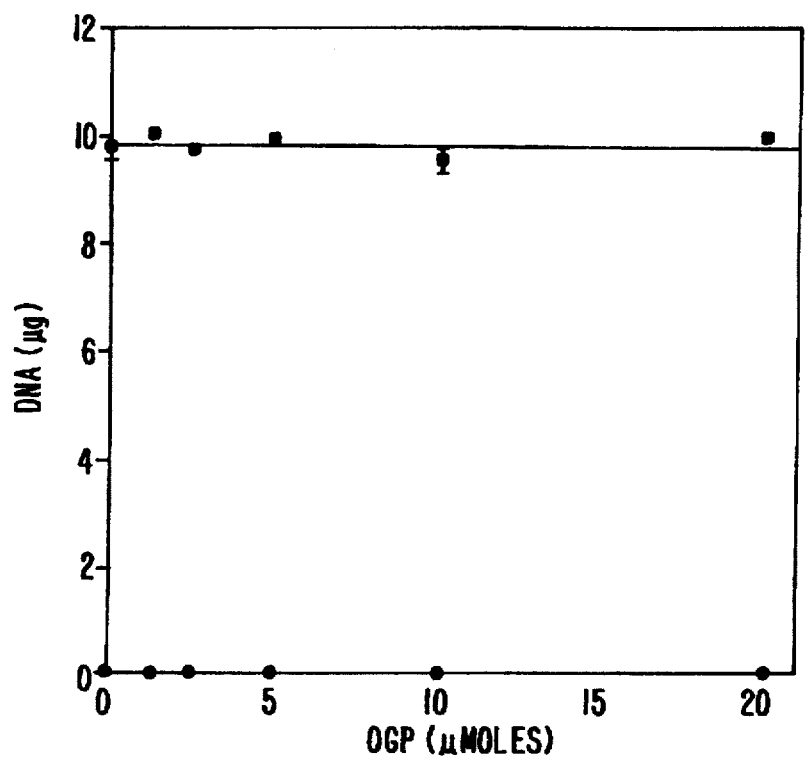
FIG. 7 illustrates the effects of increasing amounts of OGP on the recovery of plasmid DNA from the aqueous and organic phases following Bligh and Dyer extraction of lipid-nucleic acid complexes (plasmid/DODAC).
Figure 8:
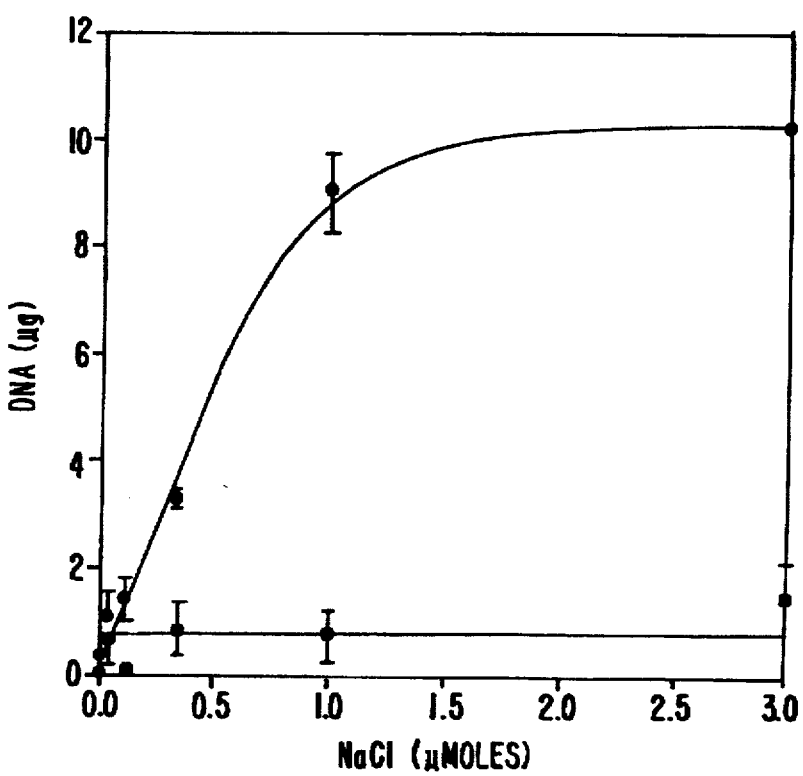
FIG. 8 shows the effects of increasing amounts of NaCl on the recovery of plasmid DNA from the aqueous phase following Bligh and Dyer extraction of lipid-nucleic acid complexes.

This example illustrates the stability of the hydrophobic, charge-neutralized lipid-nucleic acid complex in detergent solutions (FIG. 7) and instability in the presence of added salts (FIG. 8).

Plasmid DNA (10 μg) was mixed with 40 nmoles of DODAC in a Bligh and Dyer monophase as described in Example 1. OGP was added to achieve concentration up to 20 mM (20 μmoles in 1 mL) prior to separating the sample into two phases. This concentration was the maximum amount which could be added from a 2M stock solution of OGP without disrupting the monophase system. Regardless of the OGP concentration, greater than 99% of the DNA partitioned into the organic phase, demonstrating the stability of the hydrophobic, charge-neutralized complexes.

The effect of increasing concentrations of NaCl on the stability of the hydrophobic, charge-neutralized lipid-nucleic acid complex was also evaluated. As illustrated in FIG. 8, monovalent cationic lipid binding to DNA was completely inhibited in the presence of 1 μmole NaCl. At this level, $Na^+$ is present in a 25 molar excess relative to the amount of cationic lipid added. As expected, the complex between DNA and the polyvalent lipid DOSPA was more stable in the presence of NaCl. In fact, addition of $Na^+$ in a 300-fold molar excess relative to DOSPA did not cause partitioning of the charge-neutralize lipid-nucleic acid complex into the aqueous phase.

EXAMPLE 6

This example illustrates the influence of cationic lipid binding on DNA migration by agarose gel electrophoresis.

Figure 9A:
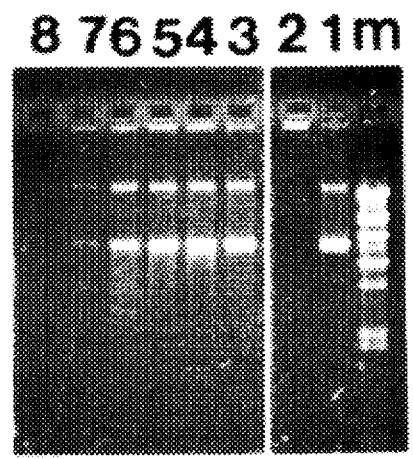
FIGS. 9A and 9B show the effect of poly-L-lysine and DODAC on the electrophoretic mobility of plasmid DNA.

FIG. 9A shows the gel mobility characteristics of the charge-neutralized lipid-nucleic acid complexes made in the presence of OGP compared to that of the poly-L-lysine condensed DNA control. Lane 2 shows that the nonlipid-based DNA/poly-L-lysine complexes exhibit significantly reduced mobility in an agarose gel. This result is consistent with studies which have demonstrated that DNA condensed with cationic liposomes adopt a macromolecular structure that does not move within an applied electric field (see, Bertling, et al., *Biotechnol. Appl. Biochem.* 13:390–405 (1991)). This effect may be a consequence of charge neutralization and/or increases in molecular size. In contrast, when DNA is mixed with cationic lipids under conditions of Example 1, there is no indication that the migration of DNA has been altered (see FIG. 9A, lanes 3–5). These studies provide further evidence suggesting that cationic lipid binding to DNA using the methods of the present invention does not result in the condensation of DNA. Changes in DNA mobility were observed, however, when the cationic lipid concentration was increase beyond cationic lipid to DNA phosphate charge ratios of 2 (see lanes 6 to 8). For example, addition of 320 nmoles of DODAC resulted in a decrease in DNA migrating into the gel and a small proportion of the DNA migrating near the top of the gel. This indicates that condensation of DNA can be achieved with excess cationic lipids.

EXAMPLE 7

This example illustrates the ability of cationic lipids to protect plasmid DNA from enzymatic digestion.

Figure 9B:
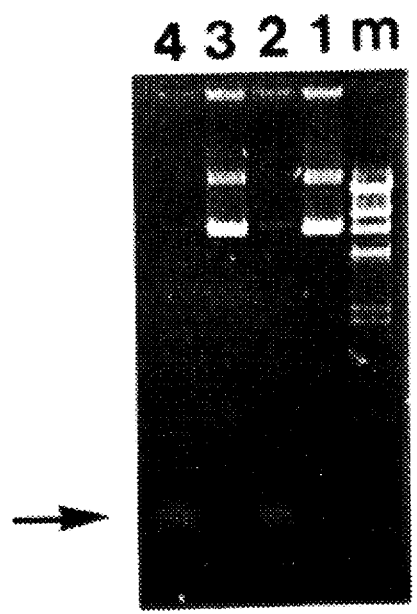

To determine the ability of cationic lipids to protect plasmid DNA from enzymatic digestion, DNase I mediated degradation of the lipid-nucleic acid complex (plasmid/DODAC complex prepared as described above) was also evaluated using agarose gel electrophoresis (see FIG. 9B). In these experiments, plasmid in OGP solution was mixed with a sufficient amount of DNase I to generate small DNA fragments after a 10 min incubation at 37° C. (lane 2). Lane 1 shows undigested plasmid as a control. Using identical conditions, the complexes (plasmid complexed with the monocationic lipid DODAC) was not protected against the enzymatic activity of DNase I (lane 4). DNA extracted from the complex in the absence of DNase I (lane 3) shows intact DNA. This provides further evidence that the nucleic acids in the lipid-nucleic acid complexes is in an uncondensed state and is susceptible to degradation.

EXAMPLE 8

This example illustrates the preparation of lipid-nucleic acid particles of β-gal, DODAC and ESM.

Figure 10A:
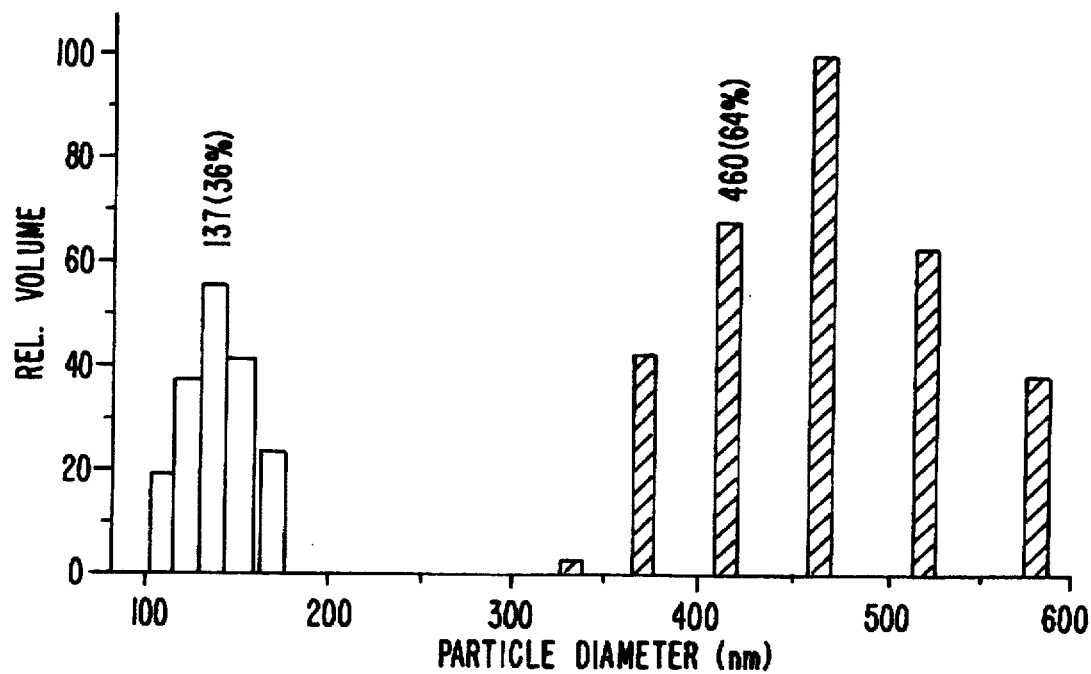
FIG. 10 is a bar graph which illustrates the QELS results of a typical lipid-nucleic acid complex mixture prepared from β-gal plasmid/DODAC/ESM.
Figure 10B:
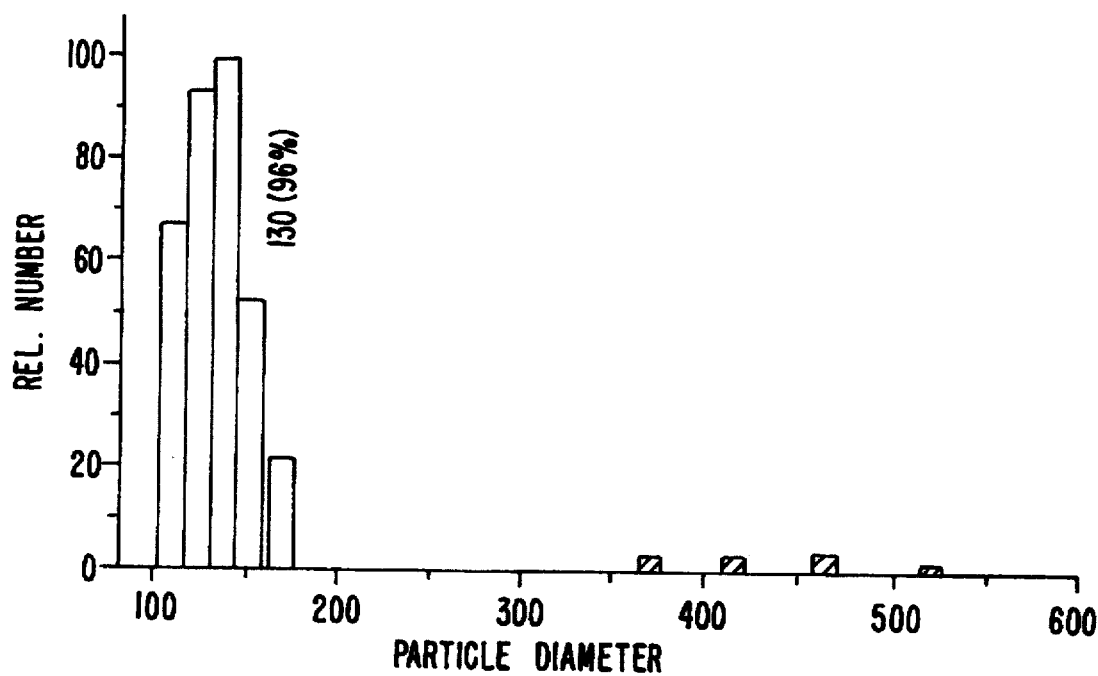

Cationic lipid DODAC, non-cationic lipid ESM, and nucleic acid β-gal plasmid were formulated using a detergent dialysis method according to the "strategy of reverse order" (see FIG. 2) as follows:

Individual solutions of DNA (10 μg in 200 μL of 200 mM aqueous OGP), DODAC (160 nmoles in 400 μL OGP) and ESM (160 nmoles in 400 μL OGP) were prepared. The ESM and DODAC solutions were each sonicated at low power at 10–20 pulses. The DNA solution was then added to the ESM solution and the mixture was allowed to incubate for 0.5 hr at room temperature. The DODAC solution was added slowly to the DNA/ESM mixture while vortexing the mixture at low speed. The resultant mixture (1 mL) was placed in a SPECTRA/POR, mwco: 12–14,000 dialysis tube (Fisher Scientific) and dialyzed against six changes of 2 L of distilled sterile water over 36 hours. Size distribution of the complexes formed was determined using quasielastic light scattering (QELS) technique (Nicomp 370 particle sizer operating at a wavelength of 632.8 nm). FIG. 10 shows that two populations of particles were observed, one group sized from 50 to 150 nm and the second sized 500 to 1000 nm. The relative numbers of each depended on the type of non-cationic lipid(s) used, the amount and concentration of the two lipid components, and the DNA/lipid ratio. About 20–40% of the relative volume of the mixture were the smaller sized complexes which accounted for over 90% of the total particle number.

EXAMPLE 9

This example illustrates the state of condensation of the DNA in the lipid-nucleic acid particle.

Figure 11:
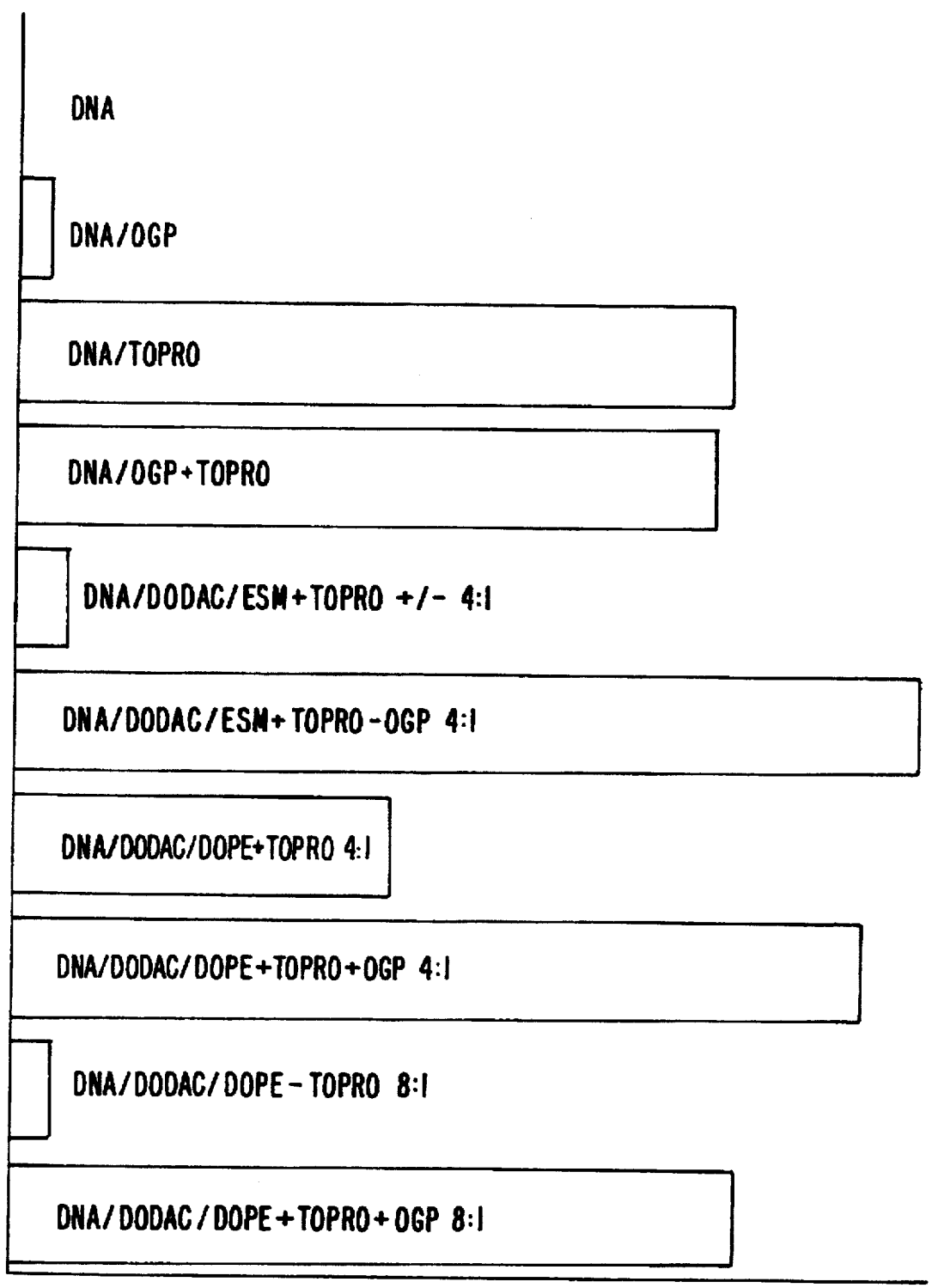
FIG. 11 is a bar graph which illustrates the fluorescence spectroscopic evaluation of DNA condensation in the lipid-nucleic acid complexes using TO-PRO-1 dye intercalation. The results show that β-gal plasmid in DODAC/ESM is condensed and protected against dye intercalation by the lipid, and that OGP can uncondense the particle.

The fluorochrome (TO-PRO-1) was used to evaluate the state of condensation of the DNA in the lipid-nucleic acid particle. A 200 μL aliquot of the lipid-nucleic acid particle (containing 2 μg plasmid DNA prepared with the protocol given in Example 8) was diluted to 1 mL with 100 mM OGP. TO-PRO-1 was added to make a final concentration of 1 μM. To measure fluorescence, spectrofluorometric measurements were performed using a Luminescence Spectrometer 50B (Perkin Elmer Ltd., Buckinghamshire, England) with an excitation wavelength of 509 nm and an emission wavelength of 533 nm. The results are presented in FIG. 11 in which the values are expressed as arbitrary fluorescence units. As FIG. 11 illustrates, plasmid DNA in lipid-nucleic acid complexes containing DODAC/ESM is condensed or protected by the lipid component. Moreover, the detergent (OGP) can dissolve the complex to uncondense the DNA (see FIG. 11).

DNA in lipid-nucleic acid particles containing DODAC/DOPE is partially accessible to TO-PRO-1 at a lipid/DNA charge ratio (+/−) of 4:1, however, at 8:1 DNA is completely protected by the lipid component. This result suggests that the nucleic acid (DNA) is partially condensed at the lower charge ratio and fully condensed at the higher ratio (FIG. 11).

EXAMPLE 10

This example demonstrates the stability of lipid-nucleic acid particles in phosphate-buffered saline and in serum containing media.

A lipid-nucleic acid particle formulation was prepared according to the procedure described in Example 8. Portions of the formulation (using either ESM or DOPE as the neutral lipid) were combined with PBS (140 mM NaCl, 10 mM $Na_2HPO_4$) or serum-containing medium and incubated for two hours at 37° C. The resulting complexes were isolated and examined for any changes in QELS size results or transfection efficiency. No difference was found for any of the formulations, indicating that the complexes were not disrupted by either sodium or serum components. One portion which was incubated with PBS for 10 days still showed very good transfection efficiency.

EXAMPLE 11

This example illustrates the protection of DNA against DNase I which is afforded by the lipid-nucleic acid particles.

Figure 12:
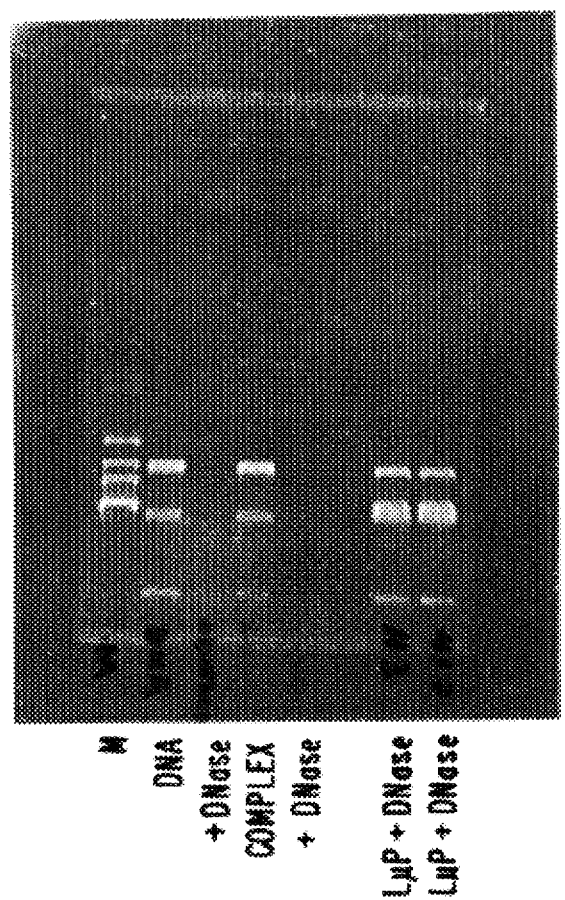
FIG. 12 shows the results of electrophoresis of DNA extracted from lipid-nucleic acid complexes following digestion with DNase I. DNA within the complex is protected from DNase I degradation whereas uncomplexed DNA is not protected.

A lipid-nucleic acid particle formulation of 10 μg DNA, 160 nmoles DODAC and 160 nmoles ESM in 1 mL total volume was prepared according to the method described in Example 8. The susceptibility of the DNA in this formulation to degradation by DNase I was evaluated by mixing the formulation with DNase I in the presence of OGP (1:1 charge ratio). The level of DNase I was equivalent to that which degrades uncomplexed DNA within 10 minutes at 37° C. The reactions were stopped after 10 min by the addition of 25 mM EDTA. DNA was extracted using the Bligh and Dyer extraction procedure in the presence of 150 mM NaCl. Under these conditions the cationic lipid/DNA complex dissociates and the resulting DNA can be efficiently recovered from the aqueous fraction. This DNA was precipitated with ⅒th volume of 3M sodium acetate (pH 5.2) and 2.5 volumes of 95% ethanol and recovered by centrifugation at 14,000 g for 30 min at 4° C. The DNA pellet was resuspended in sterile distilled water and subjected to electrophoresis on a 0.8% agarose gel (Gibco, BRL). The results are shown in FIG. 12. As FIG. 12 indicates, complexes containing ESM provide protection of DNA from DNase I degradation.

EXAMPLE 12

This example illustrates the in vitro transfection of CHO or B16 cell lines using lipid-nucleic acid particles prepared by the method of Example 8.

Figure 13:
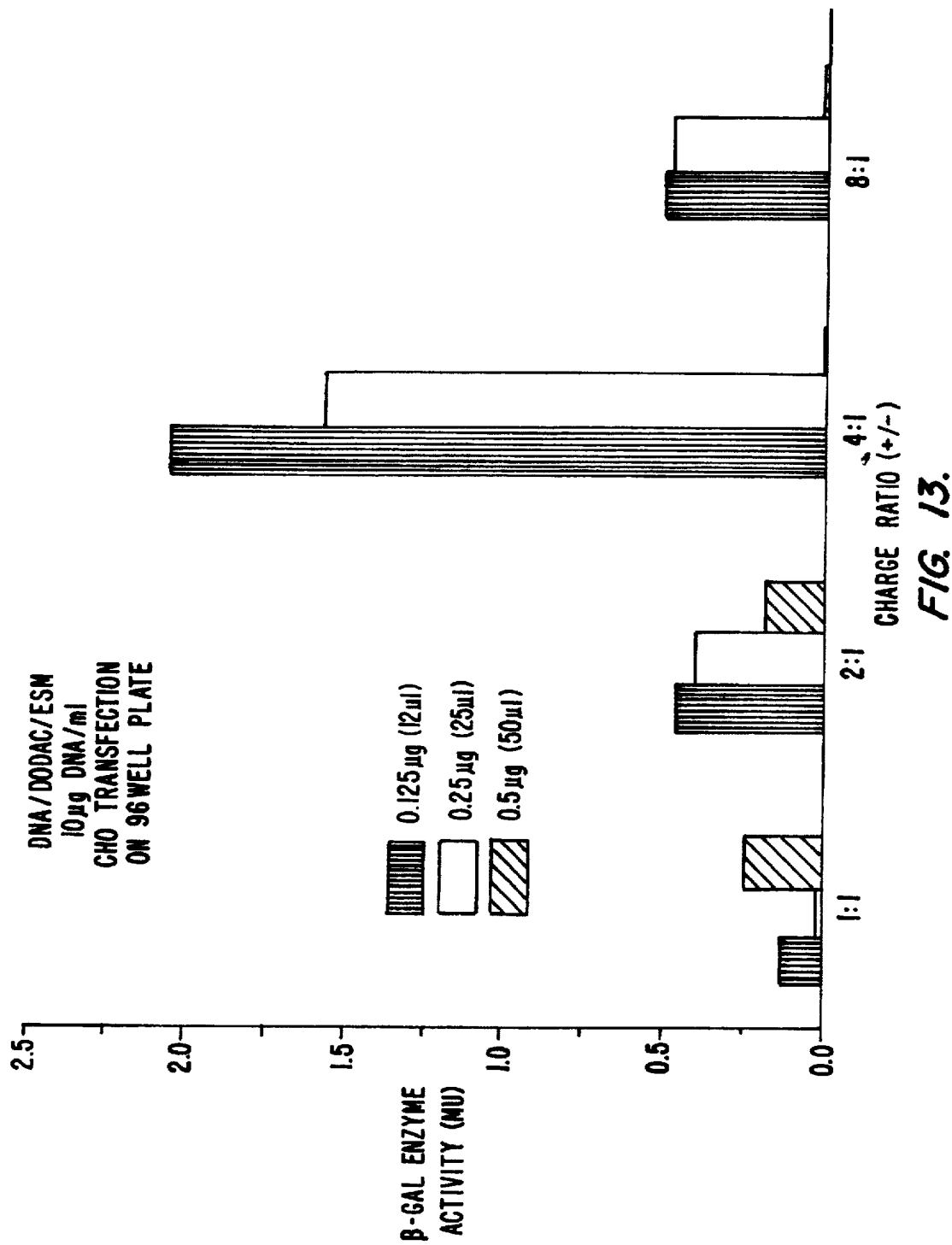
FIG. 13 provides the results of CHO cell transfection using β-gal plasmid/DODAC/ESM as assayed by β-gal enzyme activity.

In vitro transfection was performed using a 96-well cell culture plate (Costar, Cambridge, Mass., USA) containing 50% confluent growth of either Chinese Hamster Ovary (CHO) or murine melanoma (B16) cell lines. Appropriate amounts (about 6–50 μL) of the lipid-nucleic acid particle formulation (10 μg DNA/mL) were premixed with medium containing 10% serum to a final volume of 150 μL. The medium surrounding the cells was removed using a needle syringe and replaced with the lipid-nucleic acid particles in 10% serum-containing medium. The cells and complex were incubated for a further 48 hours at 37° C. The transfection efficiency was evaluated using β-gal stain or an enzyme activity assay. Results are presented in FIG. 13.

The transfection study showed excellent transfection efficiency with ESM-containing complexes and with DOPE-containing complexes (not shown). A cationic lipid to DNA charge ratio of 3:1 to 4:1 gave the best in vitro transfection results.

VII. Conclusion

As discussed above, the present invention provides novel charge-neutralized lipid-nucleic acid complexes. These hydrophobic DNA intermediates can be isolated and the DNA exists in a non-condensed form as measured by dye binding and DNase I sensitivity. These complexes can be used in the preparation of other lipid-nucleic acid particles which are effective for delivering nucleic acids to target cells.

The methods described for the preparation and uses of the various nucleic acid particles can be used with essentially any nucleic acid which can exist in a lipophilic state when complexed with an appropriate cationic lipid. Examples of some constructs include those encoding adenmine deaminase, the low density lipoprotein receptor for familial hypercholesterolemia, the CFTR gene for cystic fibrosis, galactocerebrosidase for Gaucher's disease, and dystrophin or utrophin into muscle cells for Duchenne's muscular dystrophy.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A hydrophobic lipid-nucleic acid complex consisting essentially of cationic lipids and nucleic acids, which complex binds to TO-PRO-1, and is charge neutralized and soluble in organic solvents.

2. A complex in accordance with claim 1, wherein said nucleic acid is a plasmid.

3. A complex in accordance with claim 1, wherein said cationic lipids are members selected from the group consisting of DODAC, DDAB, DOTMA, DOSPA, DMRIE, DOGS and combinations thereof.

* * * * *